US009939258B2

(12) United States Patent
Lampert et al.

(10) Patent No.: US 9,939,258 B2
(45) Date of Patent: *Apr. 10, 2018

(54) CONFOCAL SURFACE TOPOGRAPHY MEASUREMENT WITH FIXED FOCAL POSITIONS

(71) Applicant: ALIGN TECHNOLOGY, INC., San Jose, CA (US)

(72) Inventors: Erez Lampert, Rehovot (IL); Adi Levin, Nes Tziona (IL); Tal Verker, Ofra (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/593,680

(22) Filed: May 12, 2017

(65) Prior Publication Data
US 2017/0248412 A1 Aug. 31, 2017

Related U.S. Application Data

(63) Continuation of application No. 14/980,580, filed on Dec. 28, 2015, now Pat. No. 9,675,429, which is a
(Continued)

(51) Int. Cl.
*G01B 11/24* (2006.01)
*G01B 11/25* (2006.01)
(Continued)

(52) U.S. Cl.
CPC ........ *G01B 11/2513* (2013.01); *A61C 9/0053* (2013.01); *G01B 11/2518* (2013.01);
(Continued)

(58) Field of Classification Search
CPC ................................ G01B 11/24; G01B 11/25
(Continued)

(56) References Cited

U.S. PATENT DOCUMENTS 2,467,432 A  4/1949 Kesling
3,407,500 A  10/1968 Kesling
(Continued)

FOREIGN PATENT DOCUMENTS

AU  3031677 A  5/1979
AU  517102 B2  7/1981
(Continued)

OTHER PUBLICATIONS

AADR. American Association for Dental Research, Summary of Activities, Mar. 20-23,1980, Los Angeles, CA, p. 195.
(Continued)

*Primary Examiner* — Roy M Punnoose
(74) *Attorney, Agent, or Firm* — Wilson Sonsini Goodrich & Rosati

(57) ABSTRACT

An apparatus is described for measuring surface topography of a three-dimensional structure. In many embodiments, the apparatus is configured to focus each of a plurality of light beams to a respective fixed focal position relative to the apparatus. The apparatus measures a characteristic of each of a plurality of returned light beams that are generated by illuminating the three-dimensional structure with the light beams. The characteristic is measured for a plurality of different positions and/or orientations between the apparatus and the three-dimensional structure. Surface topography of the three-dimensional structure is determined based at least in part on the measured characteristic of the returned light beams for the plurality of different positions and/or orientations between the apparatus and the three-dimensional structure.

18 Claims, 11 Drawing Sheets

Related U.S. Application Data continuation of application No. 14/323,237, filed on Jul. 3, 2014, now Pat. No. 9,261,356.

(51) Int. Cl.
  *A61C 9/00* (2006.01)
  *G01S 17/08* (2006.01)
  *G02B 23/24* (2006.01)
  *G02B 3/00* (2006.01)

(52) U.S. Cl.
  CPC ............ *G01S 17/08* (2013.01); *G02B 3/0056* (2013.01); *G02B 23/2461* (2013.01)

(58) Field of Classification Search
  USPC ........................................................ 356/601
  See application file for complete search history.

(56) References Cited

U.S. PATENT DOCUMENTS

| | | |
|---|---|---|
| 3,600,808 A | 8/1971 | James |
| 3,660,900 A | 5/1972 | Lawrence |
| 3,683,502 A | 8/1972 | Melvin |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,737,084 A | 4/1998 | Ishihara |
| 5,740,267 A | 4/1998 | Echerer et al. |
| 5,742,700 A | 4/1998 | Yoon et al. |
| 5,790,242 A | 8/1998 | Stern et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |

(56) References Cited

U.S. PATENT DOCUMENTS

| | | | |
|---|---|---|---|
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,482,298 B1 | 11/2002 | Bhatnagar | |
| 6,524,101 B1 | 2/2003 | Phan et al. | |
| 6,554,611 B2 | 4/2003 | Shishti et al. | |
| 6,572,372 B1 | 6/2003 | Phan et al. | |
| 6,573,998 B2 | 6/2003 | Cohen-Sabban | |
| 6,629,840 B2 | 10/2003 | Chishti et al. | |
| 6,697,164 B1 | 2/2004 | Babayoff et al. | |
| 6,705,863 B2 | 3/2004 | Phan et al. | |
| 6,722,880 B2 | 4/2004 | Chishti et al. | |
| 6,940,611 B2 | 9/2005 | Babayoff et al. | |
| 7,092,107 B2 | 8/2006 | Babayoff et al. | |
| 7,230,725 B2 | 6/2007 | Babayoff et al. | |
| 7,319,529 B2 | 1/2008 | Babayoff | |
| 7,477,402 B2 | 1/2009 | Babayoff et al. | |
| 7,511,829 B2 | 3/2009 | Babayoff | |
| 7,561,273 B2 | 7/2009 | Stautmeister et al. | |
| 7,626,705 B2 | 12/2009 | Altendorf | |
| 7,630,089 B2 | 12/2009 | Babayoff et al. | |
| 7,724,378 B2 | 5/2010 | Babayoff | |
| 7,791,810 B2 | 9/2010 | Powell | |
| 7,796,277 B2 | 9/2010 | Babayoff et al. | |
| 7,944,569 B2 | 5/2011 | Babayoff et al. | |
| 7,990,548 B2 | 8/2011 | Babayoff et al. | |
| 8,126,025 B2 | 2/2012 | Takeda | |
| 8,310,683 B2 | 11/2012 | Babayoff et al. | |
| 8,451,456 B2 | 5/2013 | Babayoff | |
| 8,488,113 B2 | 7/2013 | Thiel et al. | |
| 8,577,212 B2 | 11/2013 | Thiel | |
| 8,638,447 B2 * | 1/2014 | Babayoff | A61B 1/24 356/609 |
| 8,638,448 B2 * | 1/2014 | Babayoff | A61B 1/24 356/609 |
| 8,675,706 B2 | 3/2014 | Seurin et al. | |
| 8,743,923 B2 | 6/2014 | Geske et al. | |
| 8,767,270 B2 | 7/2014 | Curry et al. | |
| 8,878,905 B2 | 11/2014 | Fisker et al. | |
| 9,089,277 B2 | 7/2015 | Babayoff et al. | |
| 9,261,356 B2 * | 2/2016 | Lampert | G01B 11/24 |
| 9,660,418 B2 | 5/2017 | Atiya et al. | |
| 9,675,429 B2 * | 6/2017 | Lampert | G01B 11/24 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2009/0218514 A1 | 9/2009 | Klunder et al. | |
| 2012/0081786 A1 | 4/2012 | Mizuyama et al. | |
| 2012/0092680 A1 | 4/2012 | Teodorescu et al. | |
| 2012/0147912 A1 | 6/2012 | Moench et al. | |
| 2012/0281293 A1 | 11/2012 | Gronenborn et al. | |
| 2013/0163627 A1 | 6/2013 | Seurin et al. | |
| 2013/0177866 A1 | 7/2013 | Babayoff et al. | |
| 2013/0266326 A1 | 10/2013 | Joseph et al. | |
| 2014/0104620 A1 | 4/2014 | Babayoff et al. | |
| 2015/0037750 A1 | 2/2015 | Moalem | |
| 2016/0000535 A1 | 1/2016 | Atiya et al. | |
| 2016/0003610 A1 | 1/2016 | Lampert et al. | |
| 2016/0003613 A1 | 1/2016 | Atiya et al. | |
| 2016/0015489 A1 | 1/2016 | Atiya et al. | |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 2437027 A2 | 4/2012 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | 08508174 | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-9924786 A1 | 5/1999 |
| WO | WO-0008415 A1 | 2/2000 |
| WO | WO-0037955 A2 | 6/2000 |
| WO | WO-02095475 A1 | 11/2002 |
| WO | WO-2007090865 A1 | 8/2007 |
| WO | WO-2010145669 A1 | 12/2010 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO

(56) References Cited

OTHER PUBLICATIONS

Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
BIOSTAR Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l Conf. on Holographic Systems, Components and Applications, Sep. 15, 1993, pp. 228-231.
CEREC Omnicam and CEREC Bluecam brochure. The first choice in every case. The Dental Company Sirona. 2014.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 the Computer Gives New Vision—Literally, Part 4 Bytes'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
DENTRAC Corporation, Dentrac document, pp. 4-13 (1992).
DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
Dummer, et al. Computed Radiography Imaging Based on High-Density 670 nm VCSEL Arrays. Proceedings of SPIE vol. 7557, 75570H (2010)http://vixarinc.com/pdf/SPIE_radiography_manuscript_submission1.pdf.
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

(56) References Cited

OTHER PUBLICATIONS

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries, Abstracts of Papers," J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . 22 .
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
International search report and written opinion dated Oct. 19, 2015 for PCT/IB2015/054904.
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984). KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pellin Broca Prisms—Specifications. Thor Labs. Updated Nov. 30, 2012. www.thorlabs.com.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www. essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.

(56) References Cited

OTHER PUBLICATIONS

Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information—Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile!Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
You May Be a Candidate for This Invisible No-Braces Treatment, Allesee Orthodontic Appliances-Pro Lab product information for patients, 2 pages (2002).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

\* cited by examiner

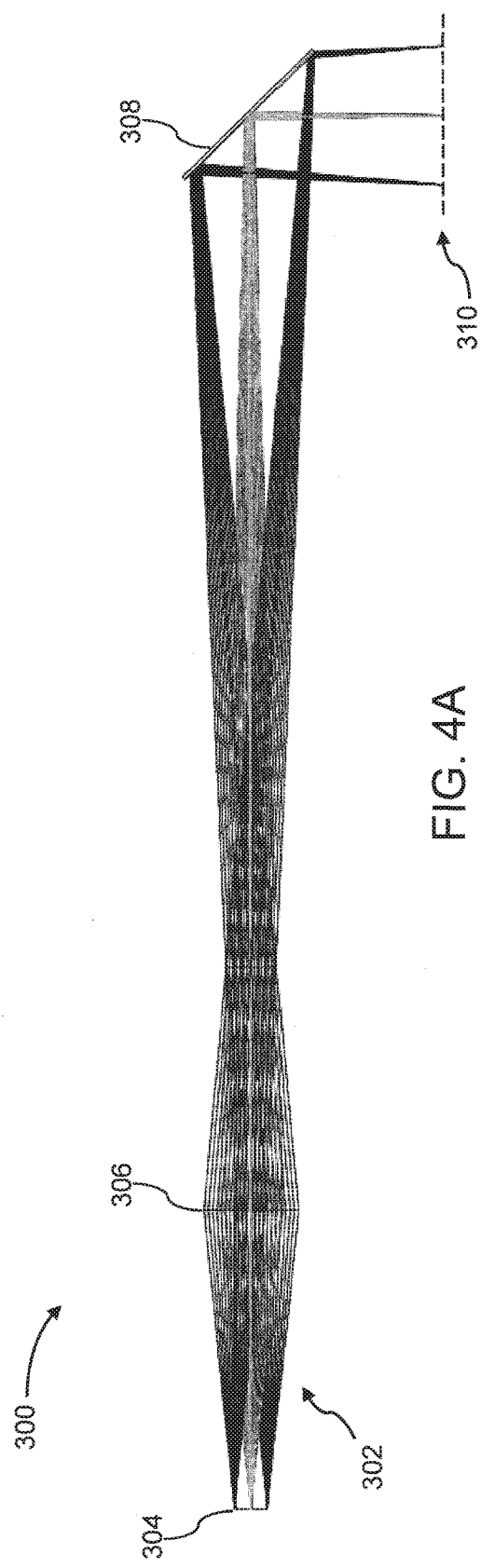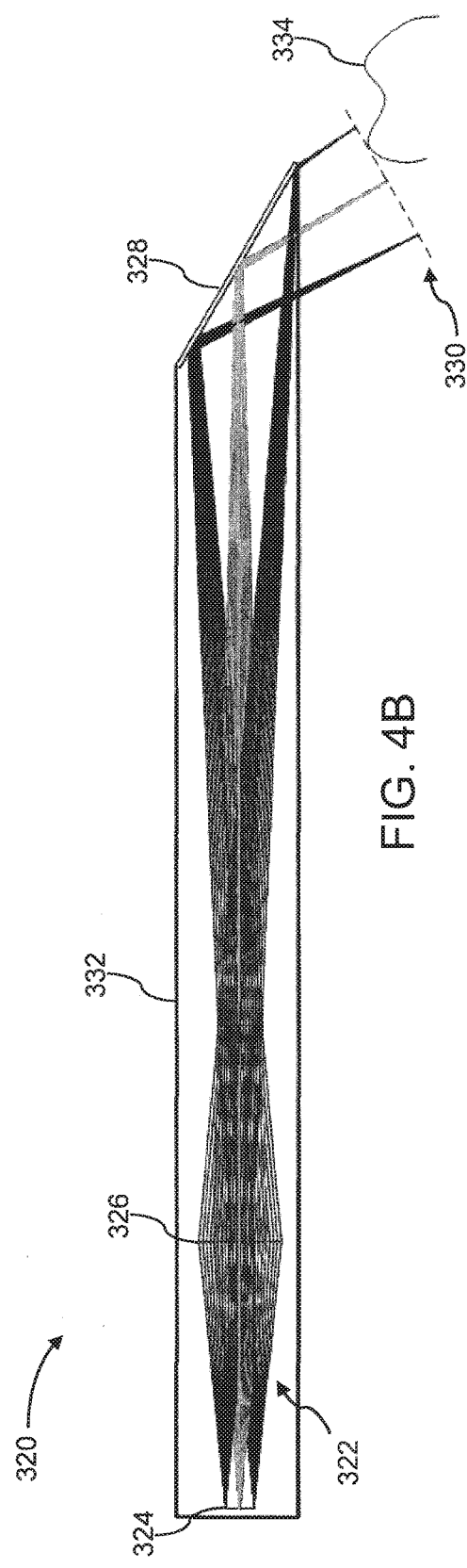

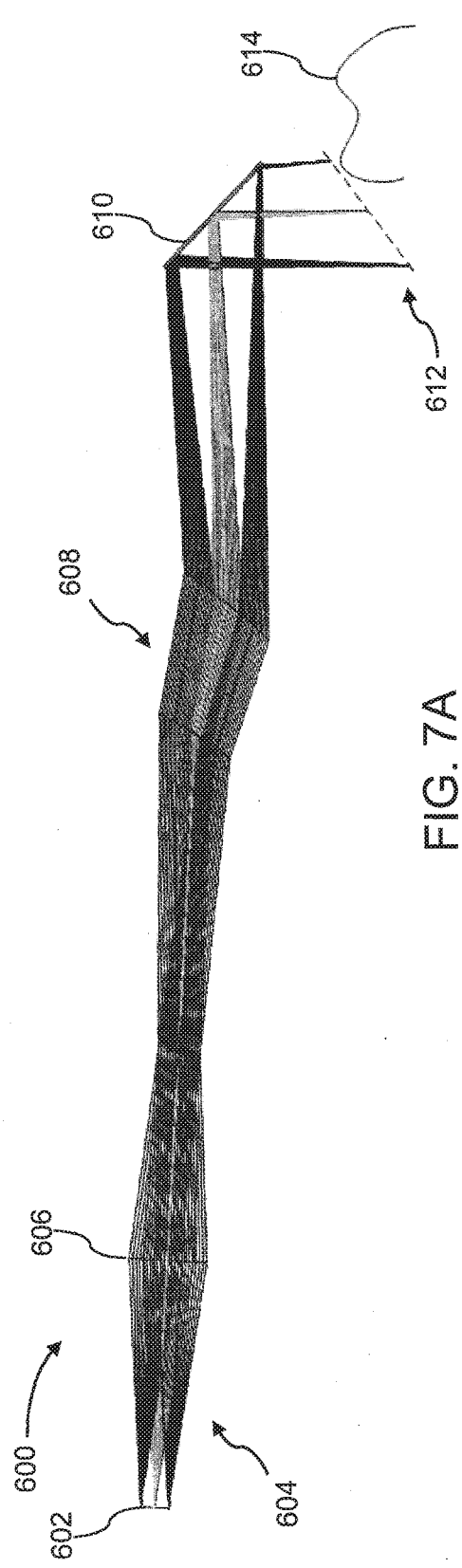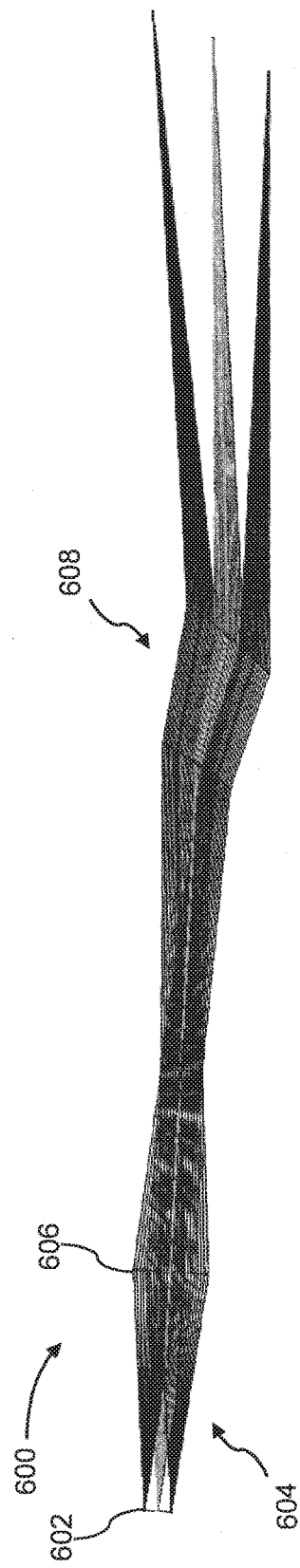
FIG. 7A
FIG. 7B

CONFOCAL SURFACE TOPOGRAPHY MEASUREMENT WITH FIXED FOCAL POSITIONS

CROSS-REFERENCE

This application is a continuation application of U.S. patent application Ser. No. 14/980,580, filed Dec. 28, 2015, now U.S. Pat. No. 9,675,429, which is a continuation application of U.S. patent application Ser. No. 14/323,237, filed Jul. 3, 2014, now U.S. Pat. No. 9,261,356, each of which are incorporated herein by reference in their entirety.

BACKGROUND

A variety of approaches have been developed for measuring surface topography optically. For example, optical systems and methods have been developed and employed that can be used to optically measure surface topography of a patient's teeth. The measured surface topography of the teeth can be used, for example, to design and manufacture a dental prosthesis and/or to determine an orthodontic treatment plan to correct a malocclusion.

One technique for measuring surface topography optically employs laser triangulation to measure distance between a surface of the tooth and an optical distance probe, which is inserted into the oral cavity of the patient. Surface topography measured via laser triangulation, however, may be less accurate than desired due to, for example, sub-optimal reflectivity from the surface of the tooth.

Other techniques for measuring surface topography optically, which are embodied in CEREC-1 and CEREC-2 systems commercially available from Siemens GmbH or Sirona Dental Systems, utilize the light-section method and phase-shift method, respectively. Both systems employ a specially designed hand-held probe to measure the three-dimensional coordinates of a prepared tooth. Both of these approaches, however, require a specific coating (i.e. measurement powder and white-pigments suspension, respectively) to be deposited on the tooth. The thickness of the coating layer should meet specific, difficult to control requirements, which can lead to inaccuracies in the measurement data.

In yet another technique, mapping of teeth surface topography is based on physical scanning of the surface by a probe and by determining the probe's position, e.g., by optical or other remote sensing means.

U.S. Pat. No. 5,372,502 discloses an optical probe for three-dimensional surveying. Various patterns are projected onto the tooth or teeth to be measured and a corresponding plurality of distorted patterns are captured by the optical probe. Each captured pattern can be used to refine the topography measurement.

SUMMARY

Apparatus and methods for measuring surface topography of a three-dimensional structure are provided. In many embodiments, an apparatus for measuring surface topography is configured to illuminate the three-dimensional structure (e.g., a patient's dentition) with light beams for a plurality of different positions and/or orientations between an optical probe of the apparatus and the three-dimensional structure. The apparatus and methods disclosed employ confocal scanning of the three-dimensional structure without optically moving the focal positions of the light beams relative to the optical probe, but instead use movement of the optical probe relative to the structure, thus enabling smaller, faster, and more cost-effective optics.

Thus, in one aspect, an apparatus is described for measuring surface topography of a three-dimensional structure. The apparatus is configured to measure a characteristic of each of a plurality of returned light beams that are generated by illuminating the three-dimensional structure with a plurality of light beams. The characteristic is measured for a plurality of different positions and/or orientations between the apparatus and the three-dimensional structure.

In another aspect, an apparatus is described for measuring surface topography of a three-dimensional structure. In many embodiments, the apparatus includes an optical probe, an optical system, and a processing unit. The optical probe is moved relative to the three-dimensional structure. The optical system focuses each of a plurality of incident light beams to a respective focal position relative to and distal to the optical probe. Returned light beams are generated by illuminating the three-dimensional structure with the incident light beams. The processing unit determines surface topography of the three-dimensional structure based at least in part on a measured characteristic of the returned light beams for a plurality of different relative positions and/or orientations between the optical probe and the three-dimensional structure.

In another aspect, a method is described for measuring surface topology of a three-dimensional structure. The method includes focusing each of a plurality of incident light beams to a respective focal point relative to and distal to an optical probe. Returned light beams are generated by illuminating the three-dimensional structure with the incident light beams. A characteristic of the returned light beams is measured for a plurality of different relative positions and/or orientations between the optical probe and the three-dimensional structure to generate surface topography data for the three-dimensional structure.

Other objects and features of the present invention will become apparent by a review of the specification, claims, and appended figures.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A illustrates an optical assembly configured to focus a plurality of light beams to respective focal positions, in accordance with many embodiments;

FIG. 4B illustrates another optical assembly configured to focus a plurality of light beams to a diagonal focal plane, in accordance with many embodiments;

FIG. 7A illustrates another optical assembly configured to focus a plurality of light beams to a diagonal focal plane, in accordance with many embodiments;

FIG. 7B illustrates an unfolded configuration of the optical assembly of FIG. 7A.

DETAILED DESCRIPTION

Figure 1A:
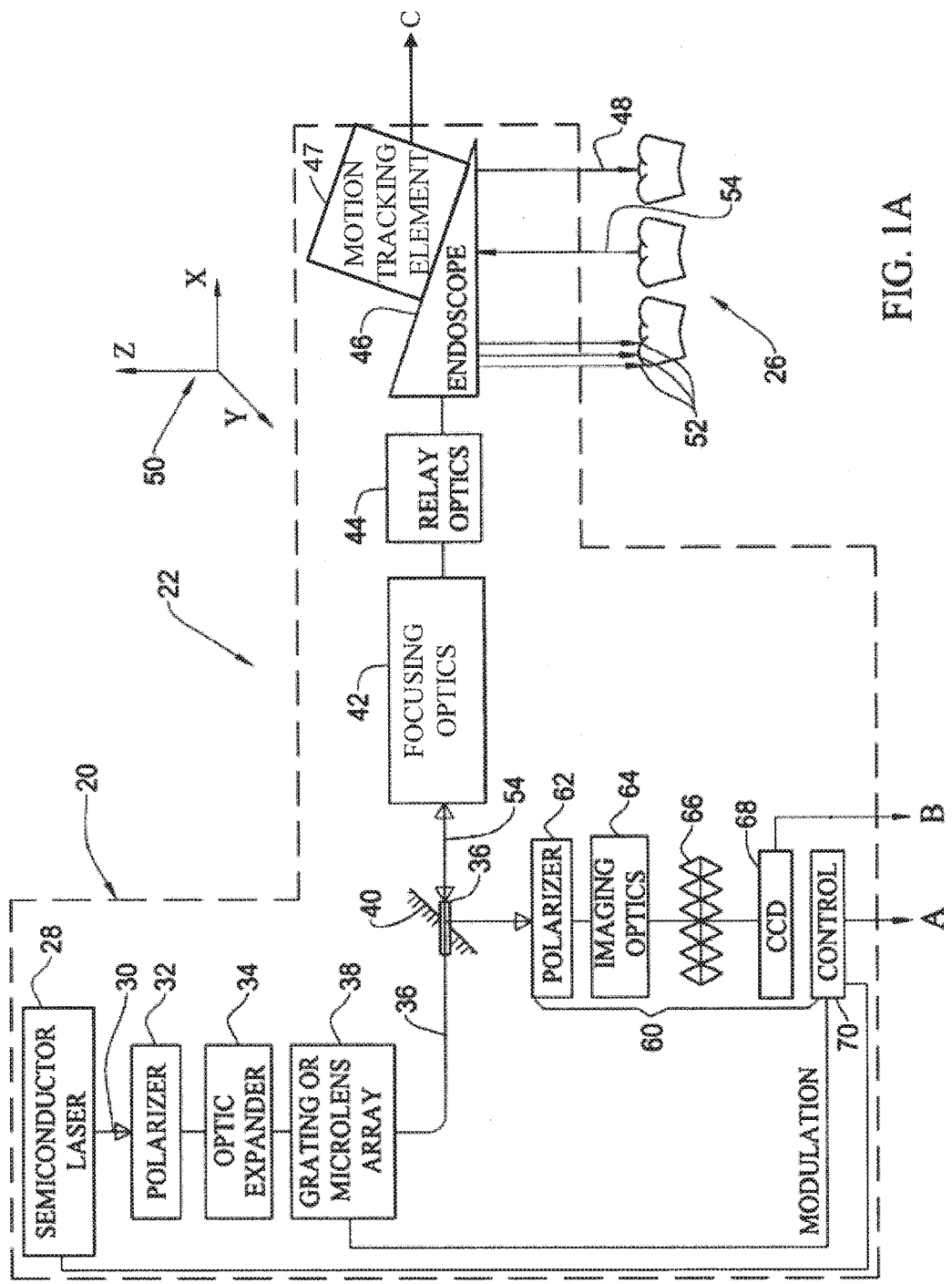
FIGS. 1A and 1B schematically illustrate, by way of a block diagram, a confocal surface topography measurement apparatus in accordance with many embodiments (FIG. 1B is a continuation of FIG. 1A)

Apparatus and methods are described herein that employ confocal measurement of surface topography. In some approaches, such as those described in U.S. Pat. No. 6,697,164, the disclosure of which is herein incorporated by reference in its entirety, incident light beams generated by a measurement apparatus are used to determine the surface topography of a three-dimensional structure. The apparatus includes an optical probe from which the light beams emanate in order to illuminate the structure. The light beams are focused by focusing optics to respective focal points (also known as focal positions) external to the optical probe. The focal positions are optically scanned through a plurality of positions relative to the optical probe in order to measure the three-dimensional surface topography. The focal positions are moved relative to the optical probe along a direction of propagation of the incident light beams (axial scanning). The focal positions can also be moved orthogonal to the direction of propagation (transverse scanning) Any description herein relating to a direction of light can be regarded as referring to a direction of the principal rays (chief rays) of the light. Similarly, any description herein relating to a direction of propagation of light can be regarded as referring to a direction of propagation of the principal rays of the light. Typically, axial and/or transverse scanning relative to the optical probe is achieved by mechanically moving an optical element, for example via suitable devices, such as galvanometric mirrors, motors, and/or telescopic scanning mechanisms. The use of such axial or transverse scanning components, however, may increase the size, weight, and cost of the measurement apparatus.

In contrast, the apparatus and methods of the present disclosure perform confocal measurement of three-dimensional surface topography without optically moving the position of the focal positions relative to the optical probe. In contrast to the above-described approaches that optically scan the focal positions relative to the optical probe, the approaches described herein focus each light beam to a respective focal point having a fixed spatial disposition relative to the optical probe. Relative movement between the optical probe and the three-dimensional structure is used to move the focal points relative to the structure. Distances between the optical probe and the three-dimensional structure are measured for a plurality of different positions and/or orientations between the optical probe and the three-dimensional structure. The data is then processed in conjunction with data regarding the relative position between the probe and the three-dimensional structure to determine surface topography of the measured structure. By avoiding the use of optical scanning mechanisms, the apparatus and methods disclosed herein may be smaller, faster, and more cost-effective relative to existing optical measurement systems.

In many embodiments, the distance between the optical probe and the three-dimensional structure is determined by measuring one or more characteristics of returning light beams generated by illuminating the structure with the incident light beams. Such characteristics can include, for example, intensity, wavelength, polarization, phase shift, interference, and/or dispersion of the returning light beams. Any description herein relating to light intensity can also be applied to other suitable characteristics of light, and vice-versa. The measurements of the characteristic(s) can be used to detect whether the incident light beams are focused on the surface of the structure and thereby determine the distance between the optical probe and the three-dimensional structure.

For example, the surface topography of the structure can be determined based on measuring the intensities of the returning light beams. In many embodiments, the apparatus is configured such that the intensity of any particular light beam returning from the structure is maximized when the incident light beam is focused on the surface of the structure. By moving the probe relative to the structure, a distance between the probe and the structure for a particular light beam and position and orientation of the probe relative to the structure can be determined by identifying when the intensity of the respective returning reflected light beam is maximized. The surface topography of the structure can then be determined based on the measured intensities of the returned light beams and the position and/or orientation of the optical probe relative to the structure.

As another example, the surface topography can be determined by using spatial frequency analysis to identify which regions of the structure are in focus. In many embodiments, focused regions will contain higher spatial frequencies than out of focus regions. Accordingly, a distance between the probe and a specified region on the structure for a particular position and orientation of the probe relative to the structure can be determined by identifying when the spatial frequencies of the region are maximized. This approach can be applied to determine the surface topography of structures having spatial details.

The apparatus and methods described herein can be used to measure the surface topography of any suitable three-dimensional structure. In many embodiments, optical measurements are taken to generate data representing the three-dimensional surface topography of a patient's dentition. The data can be used, for example, to produce a three-dimensional virtual model of the dentition that can be displayed and manipulated. The three-dimensional virtual models can be used to, for example, define spatial relationships of a patient's dentition that are used to create a dental prosthesis (e.g., a crown or a bridge) for the patient, provide a digital model or a physical model for record keeping purposes, set up a treatment plan, fabricate orthodontic appliances, or any other dental purpose. The surface topography data can be stored and/or transmitted or output, such as to a manufacturing device that can be used to, for example, make a physical model of the patient's dentition that is used by a dental technician to create a dental prosthesis for the patient.

In one aspect, an apparatus is provided for measuring surface topography of a three-dimensional structure. The apparatus can be configured to: (a) focus each of a plurality of light beams to a respective fixed focal position relative to the apparatus; (b) measure a characteristic of each of a plurality of returned light beams that are generated by illuminating the three-dimensional structure with the light beams, the characteristic being measured for a plurality of different positions and/or orientations between the apparatus and the three-dimensional structure; and (c) determine surface topography of the three-dimensional structure based at least in part on the measured characteristic of the returned light beams for the plurality of the different positions and/or orientations between the apparatus and the three-dimensional structure.

In another aspect, an apparatus is provided for measuring surface topography of a three-dimensional structure. The apparatus includes an optical probe configured to be moved relative to the three-dimensional structure. The apparatus includes an illumination unit configured to generate a plurality of incident light beams, each of the incident light beams comprising a first wavelength component. The apparatus includes an optical system configured to focus the first wavelength component of each of the plurality of incident light beams to a respective fixed focal position relative to the optical probe. The apparatus includes a detector unit configured to measure a characteristic of each of a plurality of returned light beams that are generated by illuminating the three-dimensional structure with the incident light beams. The apparatus includes a processing unit coupled with the detector unit and configured to determine surface topography of the three-dimensional structure based at least in part on the measured characteristic of the plurality of returned light beams for a plurality of different relative positions and/or orientations between the optical probe and the three-dimensional structure. In many embodiments, the characteristic is intensity.

In many embodiments, the detector unit includes a two-dimensional array of sensor elements. Each sensor element can be configured to measure the characteristic for a corresponding returned light beam of the plurality of returned light beams. The optical system can be configured to form a two-dimensional pattern of the incident light beams from light generated by the illumination unit, the two-dimensional pattern of incident light beams corresponding to the returned light beams measured by the two-dimensional array of sensor elements. The optical system can include an optics expander unit configured to expand light generated by the illumination unit to form the two-dimensional pattern of the incident light beams. The illumination unit can be configured to produce a two-dimensional pattern of the incident light beams corresponding to the returned light beams measured by the two-dimensional array of sensor elements.

The incident light beams can be focused to a plurality of respective focal lengths relative to the optical probe. In many embodiments, the incident light beams can be arranged in a plurality of rows having a first row and a last row. The incident light beams in each row can be focused to a respective common focal length. The focal lengths of the first row and the last row can be different by a predetermined length. For example, the predetermined length can be from 5 mm to 25 mm. The sensor elements can be arranged in a plane that is oriented for confocal sensing of the returned light beams relative to focal lengths of the first wavelength component of the incident light beams. In some embodiments, the plane of the sensor elements is non-orthogonal to the returned light beams.

In many embodiments, the optical probe is moved through a plurality of different positions and/or orientations relative to the structure. The three-dimensional surface topography can thus be reconstructed from the measured characteristic based at least in part on the position and/or orientation of the optical probe relative to the three-dimensional structure. Any suitable method can be used to determine the relative position and/or orientation between the optical probe and the structure. In many embodiments, the processing unit includes one or more processors and a tangible non-transitory storage device. The tangible non-transitory storage device can store instructions executable by the one or more processors to cause the one or more processors to process data of the measured characteristic generated using the detector unit for the plurality of different relative positions and/or orientations between the optical probe and the three-dimensional structure. The data can be processed by the one or more processors to determine relative position and/or orientation between the optical probe and the three-dimensional structure.

In many embodiments, the apparatus further includes a motion tracking device configured to collect motion data. The processing unit can include one or more processors and a tangible non-transitory storage device. The tangible non-transitory storage device can store instructions executable by the one or more processors to cause the one or more processors to process the motion data to determine relative position and/or orientation between the optical probe and the three-dimensional structure. For example, the motion tracking device can include a camera and the motion data can include image data. In another example, the motion tracking device can include a gyroscope and/or an accelerometer. As a further example, the motion tracking device can include an electromagnetic sensor.

Any suitable configuration of the plurality of incident light beams can be used. For example, the optical system can be configured to focus the first wavelength component of the light beams to at least 10 different focal lengths relative to the scanner, and the focal lengths can have a range of at least 10 mm.

In another aspect, a method is provided for measuring surface topography of a three-dimensional structure. The method can include generating a plurality of incident light beams, each of the incident light beams including a first wavelength component. The first wavelength component of each of the incident light beams can be focused to a respective focal position relative to an optical probe. A characteristic of each of a plurality of returned light beams that are generated by illuminating the three-dimensional structure with the incident light beams can be measured for a plurality of different relative positions and/or orientations between the optical probe and the three-dimensional structure. The measured characteristic for the plurality of different relative positions and/or orientations between the optical probe and the three-dimensional structure can be processed to generate surface topography data for the three-dimensional structure. The surface topography for the three-dimensional structure can be generated using the surface topography data. In many embodiments, the measured characteristic is intensity. In many embodiments, the method includes tracking changes in relative position and/or orientation between the optical probe and the three-dimensional structure.

The incident light beams can be arranged in a plurality of rows having a first row and a last row. For example, the incident light beams in each row can be focused to a respective common focal length. The focal lengths of the first row and the last row can be different by a predetermined length. For example, the predetermined length can be at least 10 mm. The incident light beams can be focused to any suitable respective fixed positions relative to the probe. For example, the wavelength component of the light beams can be focused to at least 10 different focal lengths relative to the scanner, and the focal lengths can have a range of at least 10 mm.

Figure 1B:
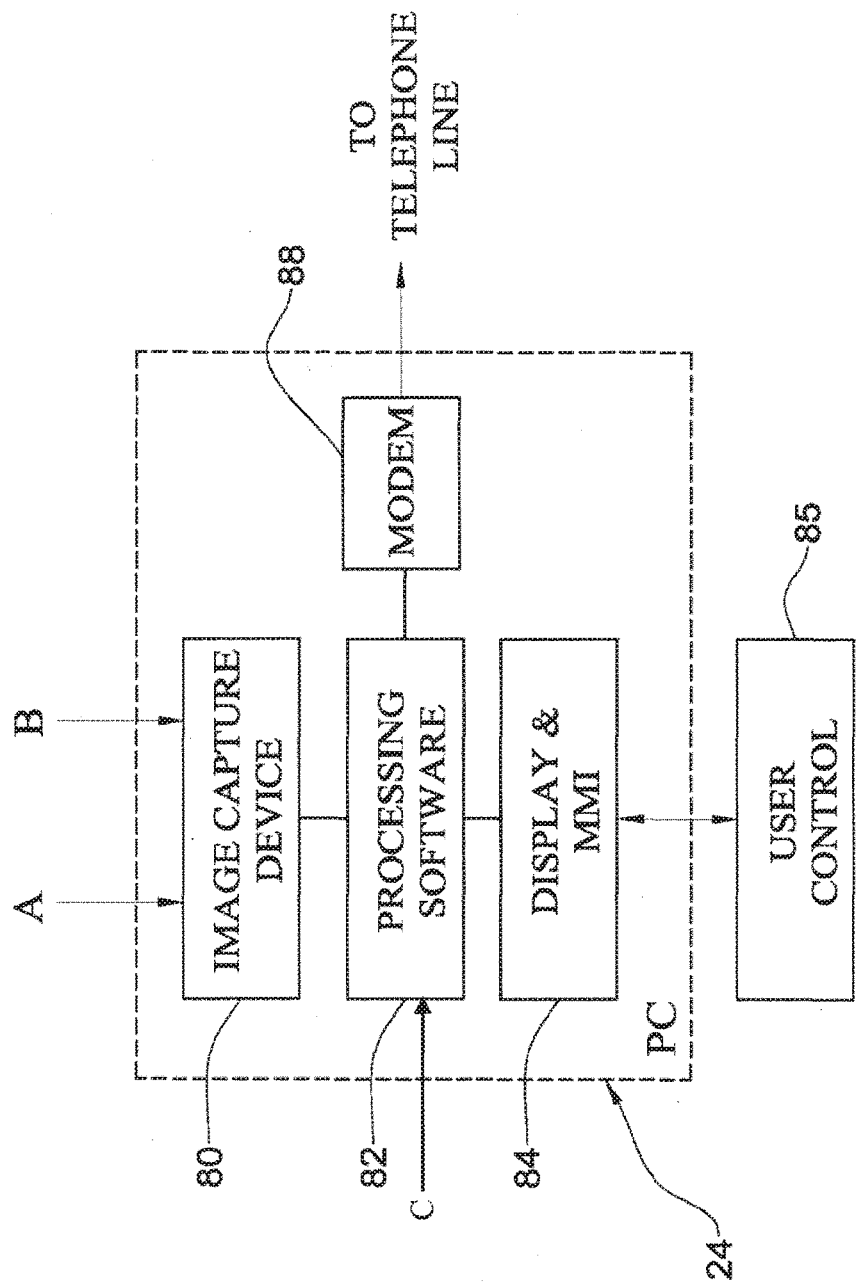

Turning now to the drawings, in which like numbers designate like elements in the various figures, FIGS. 1A and 1B illustrate an apparatus 20 for measuring surface topography optically. The apparatus 20 includes an optical device 22 coupled to a processor 24. The illustrated embodiment is particularly useful for measuring surface topography of a patient's teeth 26. For example, the apparatus 20 can be used to measure surface topography of a portion of the patient's teeth where at least one tooth or portion of tooth is missing to generate surface topography data for subsequent use in design and/or manufacture of prosthesis for the patient (e.g., a crown or a bridge). It should be noted, however, that the invention is not limited to measuring surface topography of teeth, and applies, mutatis mutandis, also to a variety of other applications of imaging of three-dimensional structure of objects (e.g., for the recordal of archeological objects, for imaging of a three-dimensional structure of any suitable item such as a biological tissue, etc.).

The optical device 22 includes, in the illustrated embodiment, a light source (e.g., semiconductor laser unit 28) emitting a light, as represented by arrow 30. The light beam 30 can include a single wavelength component or multiple wavelength components. In some instances, light with multiple wavelength components can be generated by a plurality of light sources. The light passes through a polarizer 32, which causes the light passing through the polarizer 32 to have a certain polarization. The light then enters into an optic expander 34, which increases the diameter of the light beam 30. The light beam 30 then passes through a module 38, which can, for example, be a grating or a micro lens array that splits the parent beam 30 into a plurality of light beams 36, represented here, for ease of illustration, by a single line.

The optical device 22 further includes a partially transparent mirror 40 having a small central aperture. The mirror 40 allows transfer of light from the laser unit 28 through the downstream optics, but reflects light travelling in the opposite direction. It should be noted that in principle, rather than a partially transparent mirror, other optical components with a similar function may be used (e.g., a beam splitter). The aperture in the mirror 40 improves the measurement accuracy of the apparatus. As a result of this mirror structure, the light beams produce a light annulus on the illuminated area of the imaged object as long as the area is not in focus. The annulus becomes a sharply-focused illuminated spot when the light beam is in focus relative to the imaged object. Accordingly, a difference between the measured intensity when out-of-focus and in-focus is larger. Another advantage of a mirror of this kind, as opposed to a beam splitter, is that internal reflections that occur in a beam splitter are avoided, and hence the signal-to-noise ratio is greater.

The optical device 22 further includes focusing optics 42, relay optics 44 and an endoscopic probe member 46. The focusing optics 42 can include suitable optics for focusing the light beams 36 to a plurality of respective focal points at fixed spatial dispositions relative to the probe member 46, as described below. In many embodiments, the focusing optics 42 is static, such that the optical device 22 does not employ mechanisms to scan the focal points (e.g., axially or transversely) relative to the probe member 46. In many embodiments, the relay optics 44 is configured to maintain a certain numerical aperture of the light beam's propagation.

The endoscopic probe member 46 can include a light-transmitting medium, which can be a hollow object defining within it a light transmission path or an object made of a light-transmitting material (e.g., a glass body or tube). The light-transmitting medium may be rigid or flexible (e.g., fiber optics). In many embodiments, the endoscopic probe member 46 includes a mirror of the kind ensuring total internal reflection and directing the incident light beams towards the patient's teeth 26. The endoscope 46 thus emits a plurality of incident light beams 48 impinging on to the surface of the patient's teeth 26.

The endoscope 46 can include one or more motion tracking elements 47 (e.g., a gyroscope, an accelerometer, targets for optical tracking, an electromagnetic sensor). In many embodiments, the motion tracking element 47 generates a motion tracking signal in response to movement of the endoscope 46. In many embodiments, the motion tracking signal is processed by the processor 24 to track changes in spatial disposition of the endoscope 46 in six degrees of freedom (i.e., three translational degrees of freedom and three rotational degrees of freedom).

In many embodiments, the incident light beams 48 form a two-dimensional array of light beams arranged in a plane, relative to a Cartesian reference frame 50, and propagating along the Z-axis. The light beams 48 can be focused to respective focal points defining a suitable focal plane, such as a plane orthogonal to the Z axis (e.g., an X-Y plane) or a non-orthogonal plane. When the incident light beams 48 are incident upon an uneven surface, the resulting array of illuminated spots 52 are displaced from one another along the Z-axis, at different $(X_i, Y_i)$ locations. Thus, while an illuminated spot 52 at one location may be in focus for a given relative spatial disposition between the endoscope 46 and the teeth 26, illuminated spots 52 at other locations may be out-of-focus. Therefore, the light intensity of the returned light beams of the focused spots will be at its peak, while the light intensity at other spots will be off peak. Thus, for each illuminated spot, light intensity is measured for different relative spatial dispositions between the endoscope 46 and the teeth 26. Typically, the derivative of the intensity over time will be made, and the relative spatial disposition(s) between the endoscope 46 and the teeth 26 wherein the derivative equals zero can be used to generate data that is used in conjunction with the relative spatial dispositions between the endoscope 26 and the teeth 26 to determine surface topography of the teeth. As pointed out above, as a result of use of the mirror with aperture 40, the incident light forms a light disk on the surface when out of focus and a sharply-focused light spot only when in focus. Consequently, the distance derivative will exhibit a larger change in magnitude when approaching an in-focus position, thus increasing accuracy of the measurement.

The light reflected from each of the illuminated spots 52 includes a beam travelling initially in the Z-axis in the opposite direction of the optical path traveled by the incident light beams. Each returned light beam 54 corresponds to one of the incident light beams 36. Given the asymmetrical properties of mirror 40, the returned light beams 54 are reflected in the direction of a detection assembly 60. The detection assembly 60 includes a polarizer 62 that has a plane of preferred polarization oriented normal to the polarization plane of polarizer 32. The returned polarized light beam 54 pass through imaging optics 64, typically a lens or a plurality of lenses, and then through an array of pinholes 66. Each returned light beam 54 passes at least partially through a respective pinhole of the array of pinholes 66. A sensor array 68, which can be a charge-coupled device (CCD) or any other suitable image sensor, includes a matrix of sensing elements. In many embodiments, each sensing element represents a pixel of the image and each sensing element corresponds to one pinhole in the array 66.

The sensor array 68 is connected to an image-capturing module 80 of the processor unit 24. The light intensity measured by each of the sensing elements of the sensor array 68 is analyzed, in a manner described below, by the processor 24. Although the optical device 22 is depicted in FIGS. 1A and 1B as measuring light intensity, the device 22 can also be configured to measure other suitable characteristics (e.g., wavelength, polarization, phase shift, interference, dispersion), as previously described herein. In many embodiments, the plane of the sensor array 68 is orthogonal to the returned light beams 54 (e.g., orthogonal to a direction of propagation of the returned light beams). In some embodiments, the plane of the sensor array 68 is non-orthogonal to the returned light beams 54, as described below.

The optical device 22 includes a control module 70 that controls operation of the semi-conducting laser 28. The control module 70 synchronizes the operation of the image-capturing module 80 with the operation of the laser 28 during acquisition of data representative of the light intensity (or other characteristic) from each of the sensing elements. The intensity data and data of relative spatial dispositions between the endoscope 46 and the teeth 26 are processed by the processor 24 per processing software 82 to obtain data representative of the three-dimensional topography of the external surfaces of the teeth 26. Exemplary embodiments of methods for processing the data of the characteristic and relative spatial disposition data are described below. A resulting three-dimensional representation of the measured structure can be displayed on a display 84 and manipulated for viewing (e.g., viewing from different angles, zooming-in or out) by a user control module 85 (typically a computer keyboard). In addition, the data representative of the surface topography can be transmitted through an appropriate data port such as, for example, a modem 88 or any suitable communication network (e.g., a telephone network, the Internet) to a recipient (e.g., to an off-site CAD/CAM apparatus).

By capturing relative distance data between the endoscope 46 and the structure being measured for different relative spatial dispositions between the endoscope 46 and the structure (e.g., in the case of a teeth segment, from the buccal direction, lingual direction and/or optionally from above the teeth), an accurate three-dimensional representation of the structure can be generated. The three-dimensional data and/or the resulting three-dimensional representation can be used to create a virtual model of the three-dimensional structure in a computerized environment and/or a physical model fabricated in any suitable fashion (e.g., via a computer controlled milling machine, a rapid prototyping apparatus such as a stereolithography apparatus or 3D printing apparatus).

Figure 2A:
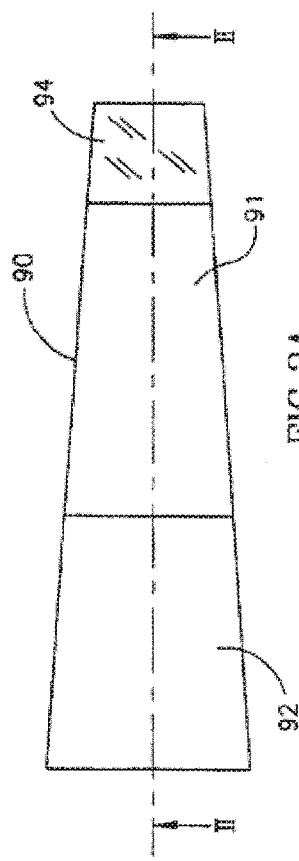
FIG. 2A is a top view of a probing member of a confocal surface topography measurement apparatus, in accordance with an embodiment.
Figure 2B:
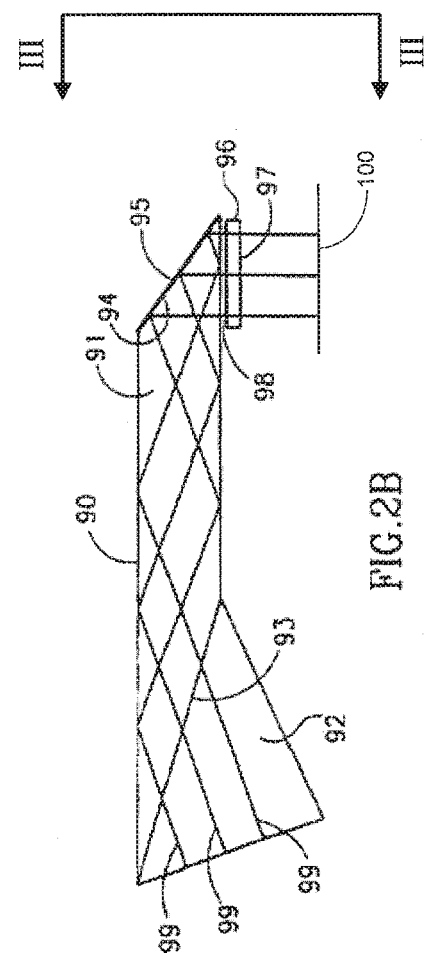
FIG. 2B is a longitudinal cross-section through the probing member of FIG. 2A, depicting exemplary rays passing therethrough.
Figure 2D:
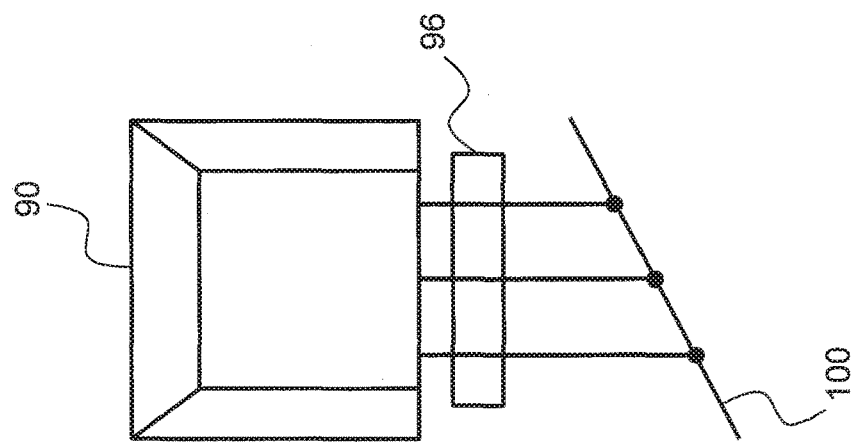
FIGS. 2C and 2D are end views of the probing member of FIG. 2A, in accordance with many embodiments.
Figure 2C:
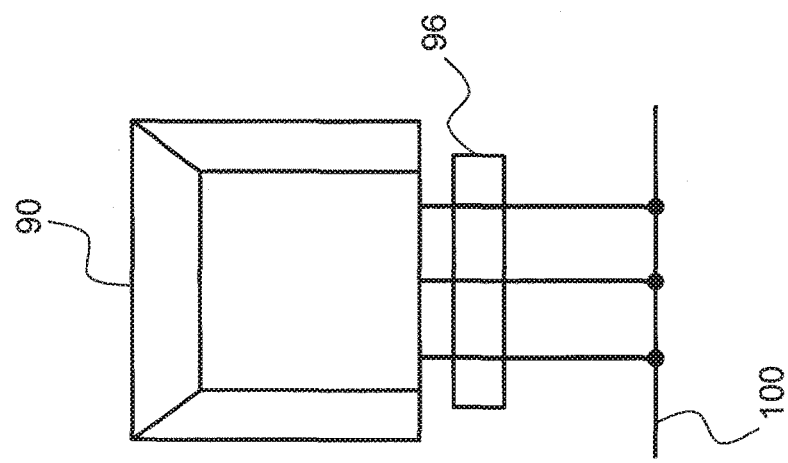

Referring now to FIGS. 2A and 2B, a probing member 90 is illustrated in accordance with many embodiments. In many embodiments, the probing member 90 forms at least a portion of the endoscope 46. The probing member 90 can be made of a light transmissive material (e.g., glass, crystal, plastic, etc.) and includes a distal segment 91 and a proximal segment 92, tightly glued together in an optically transmissive manner at 93. A slanted face 94 is covered by a reflective mirror layer 95. A transparent disk 96 (e.g., made of glass, crystal, plastic, or any other suitable transparent material) defining a sensing surface 97 is disposed along the optical path distal to the mirror layer 95 so as to leave an air gap 98 between the transparent disk 96 and the distal segment 91. The transparent disk 96 is fixed in position by a holding structure (not shown). Three light rays 99 are represented schematically. As can be seen, the light rays 99 reflect from the walls of the probing member 90 at an angle in which the walls are totally reflective, reflect from the mirror layer 95, and then propagate through the sensing face 97. While the light rays 99 can be focused external to the probing member 90 with any suitable combination of respective focal lengths, in many embodiments, the light rays 99 are focused on a focusing plane 100 external to the probing member 90. For example, as illustrated in FIG. 2C, which shows an end view III-III of the probing member 90, the light rays 99 are focused to a common focal length, thereby being focused on a focusing plane 100 that is perpendicular to the direction of propagation of the light rays 99 external to the probing member 90 (also referred to herein as the Z-axis). As another example, as illustrated in FIG. 2D, which shows an end view III-III of the probing member 90, the light rays 99 are focused to different focal lengths so as to be focused on a focusing plane 100 that is non-perpendicular to the Z-axis. While two configurations of focal positions are illustrated and described, any suitable configuration of focal positions can be employed.

Figure 3A:
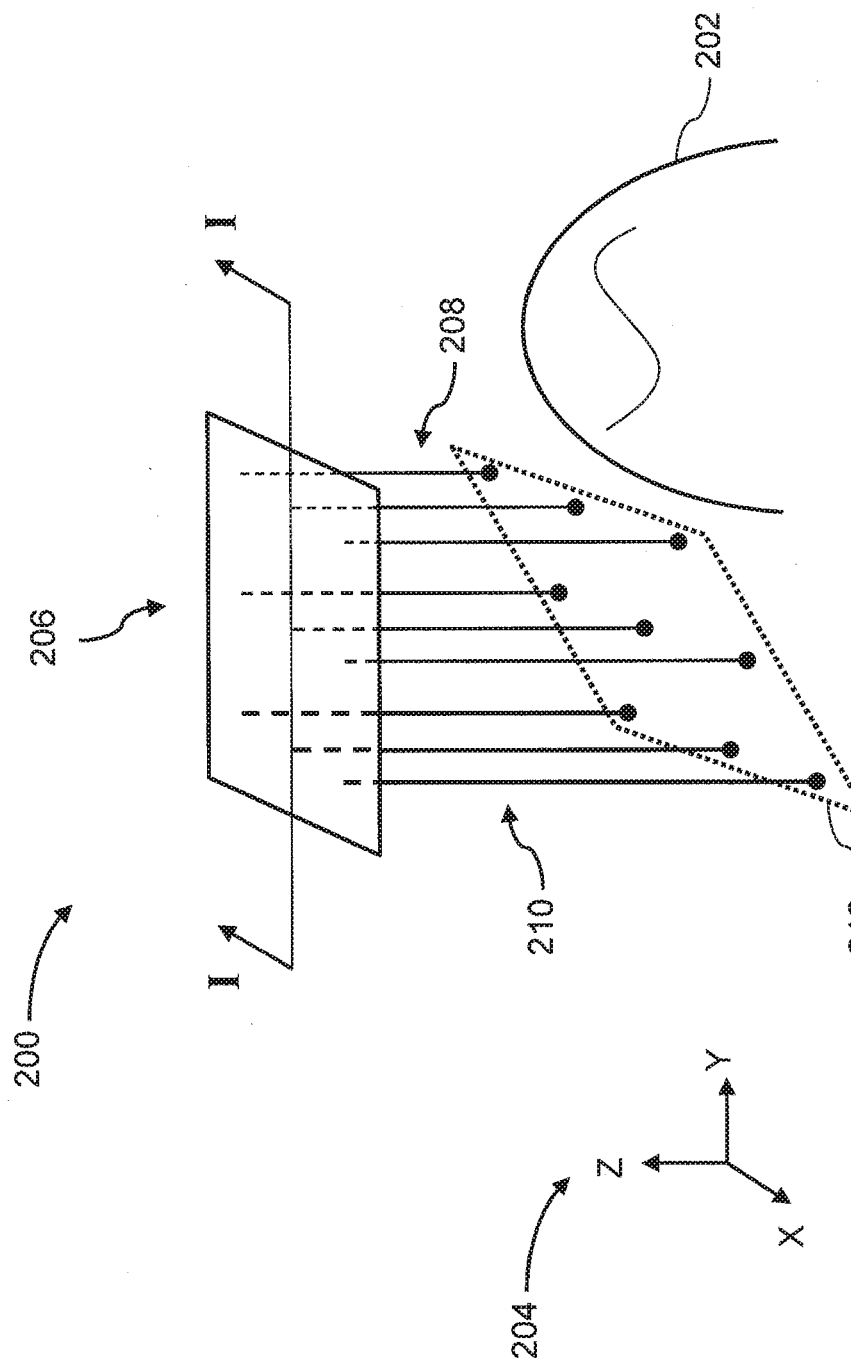
FIG. 3A illustrates an optical probe scanning a structure using fixed focal positions, in accordance with many embodiments.
Figure 3B:
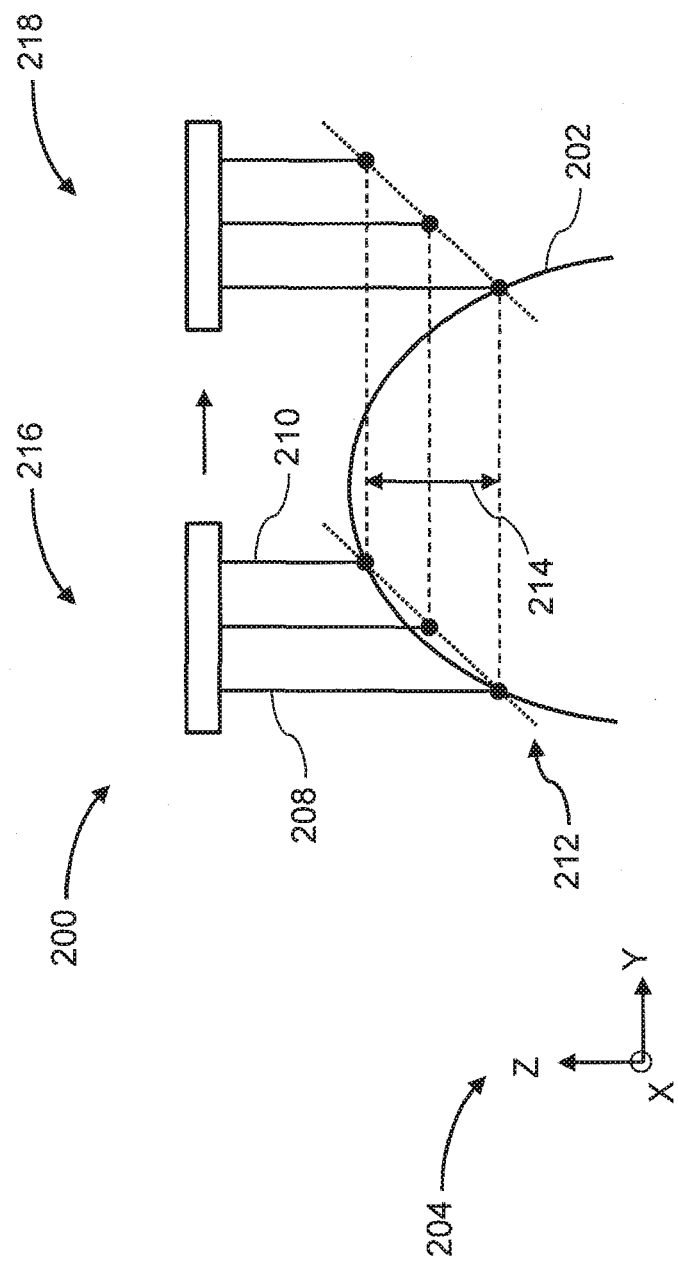
FIG. 3B shows another view of the optical probe of FIG. 3A during scanning of the structure using fixed focal positions.

FIGS. 3A and 3B illustrate an optical probe 200 scanning a structure 202 in a global Cartesian reference frame 204, in accordance with many embodiments. (FIG. 3B shows the cross-sectional view I-I as defined in FIG. 3A). The optical probe 200 can be used with any suitable scanning device or system described herein, such as the optical device 22. A two-dimensional array of incident light beams 206 emanating from the optical probe 200 are arranged in a plurality of rows extending in the X direction, including a first row 208 and a last row 210. Each row of the array of light beams 206 is focused to a respective common focal length along the Z direction, thereby forming a diagonal focal plane 212. The focal lengths of the first row 208 and the last row 210 differ by a predetermined length 214 in the Z direction. The optical probe 200 can be moved relative to the structure 202 to scan the structure 202 with the light beams 206. For example, as depicted in FIG. 3B, the optical probe 200 can be translated in the Y direction from a first position 216 to a second position 218.

In many embodiments, each row in the array of light beams 206 is focused to a different depth along the Z direction so as to produce a focal plane 212 that is not orthogonal to the Z-axis. Therefore, as the optical probe 200 is moved relative to the structure 202, the focal plane 212 of the light beams 206 sweeps through a three-dimensional volume of the structure 202. For example, as the optical probe 200 translates from position 216 to position 218, the focal plane 212 sweeps a three-dimensional volume having a Z depth 214. Accordingly, the optical probe 200 can scan the structure 202 in the Z direction through continuous movement of the optical probe 200 relative to structure 202, while maintaining constant respective focal lengths of the light beams 206. Although FIG. 3B depicts movement of the optical probe 200 in the Y direction, in many embodiments, the optical probe 200 can be moved with six degrees of freedom (e.g., three degrees of freedom in translation and three degrees of freedom in rotation) to a plurality of different relative positions and/or orientations between the optical probe 200 and the structure 202.

The array of light beams 206 can be provided in any suitable configuration. For example, the array of light beams 206 can be focused to any suitable number of different focal lengths relative to the optical probe 200, such as 3, 5, 10, 50, or 100 or more different focal lengths. The focal lengths of the array of light beams 206 can be configured to have any suitable range, such as at least 5 mm, 7.5 mm, or 10 mm or more. The focal lengths of the first row 208 and the last row 210 in the array of light beams 206 can be different by any suitable length, such as by 5 mm or less, 10 mm, 15 mm, or 25 mm or greater. For example, the focal lengths can be different by a length within the range of 5 mm to 25 mm.

The array of light beams 206 can be generated by any system or device suitable for focusing a wavelength component of each of the light beams to a respective focal position (e.g., a diagonal focal plane 212). In many embodiments, one or more optics of the optical device 22 can be used to focus an array of light beams to a plurality of fixed focal positions relative to the probe. For example, suitable embodiments of the optics described herein can be included within the grating or micro lens array 38, focusing optics 42, relay optics 44, optics within the endoscope 46, or suitable combinations thereof. The optics can be configured to be used with telecentric and/or non-telecentric confocal focusing optics.

FIG. 4A illustrates an optical assembly 300 for focusing a plurality of light beams to respective focal positions, in accordance with many embodiments. In the optical assembly 300, an array of light beams 302 emanate from a source array 304 (e.g., a micro lens array), are focused by focusing optics 306, and reflect off a mirror 308 (e.g., a mirror disposed within an endoscopic probing member) to form a focal plane 310. The mirror 308 can be positioned at a 45° angle relative to the optical axis in order to produce an orthogonal focal plane 310.

FIG. 4B illustrates an optical assembly 320 for focusing a plurality of light beams to a diagonal focal plane, in accordance with many embodiments. Similar to the optical assembly 300, the system 320 includes a source array 324 that produces an array of light beams 322, focusing optics 326, and a mirror 328. The mirror 328 is tilted at a suitable angle relative to the optical axis, such as a 30° angle, in order to produce a focal plane 330 that is inclined relative to the scanner 332. The focal plane 330 can be used to scan a three-dimensional structure, such as a tooth 334, using fixed focal positions as described herein.

Figure 5:
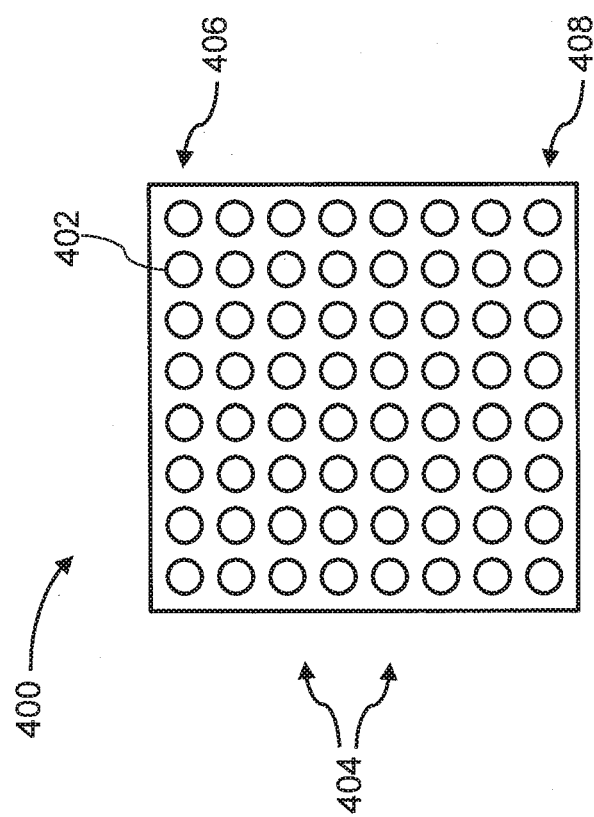
FIG. 5 illustrates a micro lens array for focusing an array of light beams to a diagonal focal plane, in accordance with many embodiments.

FIG. 5 illustrates a micro lens array 400 for focusing an array of light beams to a diagonal focal plane, in accordance with many embodiments. The micro lenses (e.g., micro lens elements 402) of micro lens array 400 are arranged in a plurality of rows 404, including a first row 406 and a last row 408. Each row of micro lenses is configured to focus light beams to a different focal length, thereby producing a diagonal focal plane.

Figure 6A:
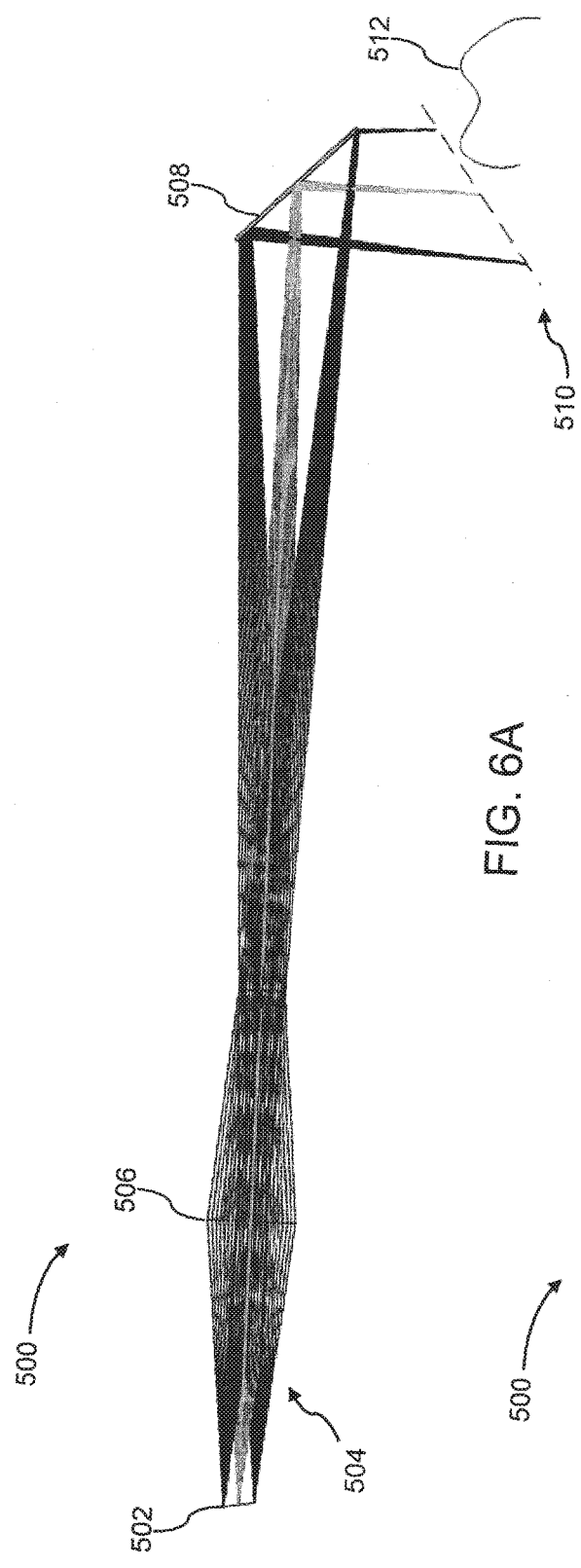
FIG. 6A illustrates another optical assembly configured to focus a plurality of light beams to a diagonal focal plane, in accordance with many embodiments.
Figure 6B:
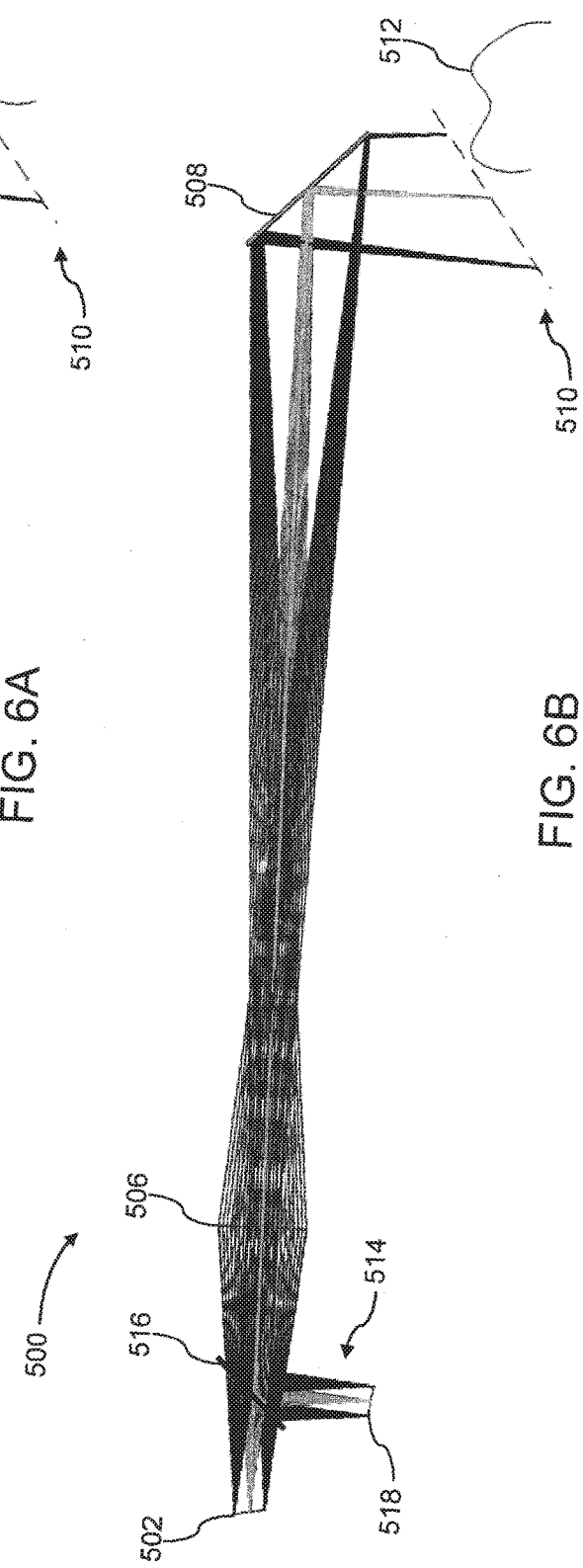
FIG. 6B illustrates the optical path of returning light beams through the optical assembly of FIG. 6A, in accordance with many embodiments.

FIG. 6A illustrates an optical assembly 500 for focusing a plurality of light beams to a diagonal focal plane, in accordance with many embodiments. The optical assembly 500 includes a tilted source array 502, which can be a micro lens array tilted at a suitable angle relative to the optical axis. The array of light beams 504 produced by the tilted source array 502 passes through focusing optics 506, and reflects off mirror 508 to form a diagonal focal plane 510, suitable for scanning the structure 512 with fixed focal positions as described herein. FIG. 6B illustrates the optical path of returned light beams 514 through the optical assembly 500. The returned light beams 514 reflected from the structure 512 pass back through the focusing optics 506, and are directed by beam splitter 516 onto the sensor array 518. As previously described, the sensor array 518 can include a plurality of sensor elements arranged in a plane. In many embodiments, the sensor array 518 is non-orthogonal relative to the returned light beams 514, such that the plane of sensor elements is tilted relative to the direction of propagation of the returned light beams 514. The plane can be tilted by the same amount as the source array 502 in order to allow for confocal sensing of the returned light beams 502.

FIG. 7A illustrates an optical assembly 600 for focusing a plurality of light beams to a diagonal focal plane, in accordance with many embodiments. FIG. 7B illustrates an unfolded configuration of the optical assembly 600. In the optical assembly 600, an array of light beams 604 emanating from a source array 602 pass through focusing optics 606. A non-symmetric optics 608 is disposed between the focusing optics 606 and a mirror 610 and configured to focus the light beams to a diagonal focal plane 612 suitable for scanning the structure 614 with fixed focal positions as described herein. Any suitable optical element or combination of optical elements can be used for the non-symmetric optics 608. For example, the non-symmetric optics 608 can include an off-axis lens tilted at a suitable angle relative to the optical axis. Alternatively or in combination, the non-symmetric optics 608 can include a Fresnel lens including a plurality of segments configured to refract each of the plurality of light beams to a respective focal position in order to produce a suitable diagonal focal plane.

The global surface topography of the structure can be reconstructed by spatially aligning the local intensity data to each other. In many embodiments, the relative position and/or orientation between the optical probe and the structure during the scanning procedure is used to determine the spatial relationships between the intensity data and thereby align the data. Any suitable method or combination of methods can be used to track the position and/or orientation of the optical probe or a suitable portion of the optical probe (e.g., the scanning tip of the endoscope 46 or probing member 90) relative to the structure, such as a suitable motion estimation or motion tracking method. For example, one or more motion tracking devices can be used to generate motion data suitable for determining the position and/or orientation of the optical probe relative to the three-dimensional structure.

In many embodiments, an optical tracking method is used to determine the spatial disposition of the probe relative to the structure with respect to six degrees of freedom. For example, the motion tracking device can include an external camera (or any other suitable image sensor) to generate image data of the probe as it is moved between a plurality of different positions and/or orientations during the scanning procedure. The camera can capture images of any suitable portion of the probe, such as a portion positioned outside of the patient's intraoral cavity. Alternatively or in combination, the camera can capture images of one or more suitable markers (e.g., included in motion tracking element 47) placed on one or more suitable portions of the probe. The images can be processed to estimate the position and/or orientation of the probe relative to the structure using any suitable machine vision method (e.g., a structure from motion algorithm, a photogrammetric method, an image registration/alignment method, and/or an optical flow estimation method such as a Lucas-Kanade method). Optionally, a camera can be integrated into or coupled with the probe, such that image data captured by the camera can be analyzed using a suitable ego-motion estimation method, such as the machine vision methods described herein, to determine the position and/or orientation of the probe relative to the structure.

Alternatively or in combination, the motion tracking device can utilize inertial-based estimation methods to determine the relative position and/or orientation of the probe. For example, the motion sensor can include an inertial measurement unit, such as an inertial sensor. The inertial sensor can be a micro electromechanical system (MEMS) device. In many embodiments, the inertial sensor includes a plurality of accelerometers and/or a plurality of gyroscopes configured to detect motion of the probe with respect to three degrees of translation and/or three degrees of rotation.

In another example, an electromagnetic tracking (EMT) system can be used to track the position and/or orientation of the probe relative to the structure. For instance, an EMT field can be provided by a suitable generator or transmitter, and the position and/or orientation of an EMT sensor within the field (e.g., with respect to up to three degrees of freedom in rotation and three degrees of freedom in translation) can be determined based on the electromagnetic signals detected by the sensor. Any suitable number and configuration of EMT field generators and EMT sensors can be used. For example, an EMT field generator can be situated at a fixed location at the site of the scanning procedure (e.g., coupled to an operating table or patient chair) and an EMT sensor can be disposed on the probe (e.g., included in motion tracking element 47) to track the motion of the probe. In many embodiments, EMT sensors are also be placed on or near the three-dimensional structure (e.g., on a patient's head, face, jaw, and/or teeth) in order to account for any motion of the structure during the measurement procedure. Alternatively or in combination, the EMT field generator can be placed on the structure and used to track the relative motion of a probe having a coupled EMT sensor. Conversely, the EMT field generator can be located on the probe and the EMT sensor can be located on the structure.

Any suitable method can be used to process the motion data to determine the position and/or orientation of the probe relative to the structure. For example, the data can be processed using a motion tracking algorithm combined with a Kalman filter. Optionally, the processing can utilize motion data received from a plurality of the different types of motion tracking systems and devices described herein.

Figure 8:
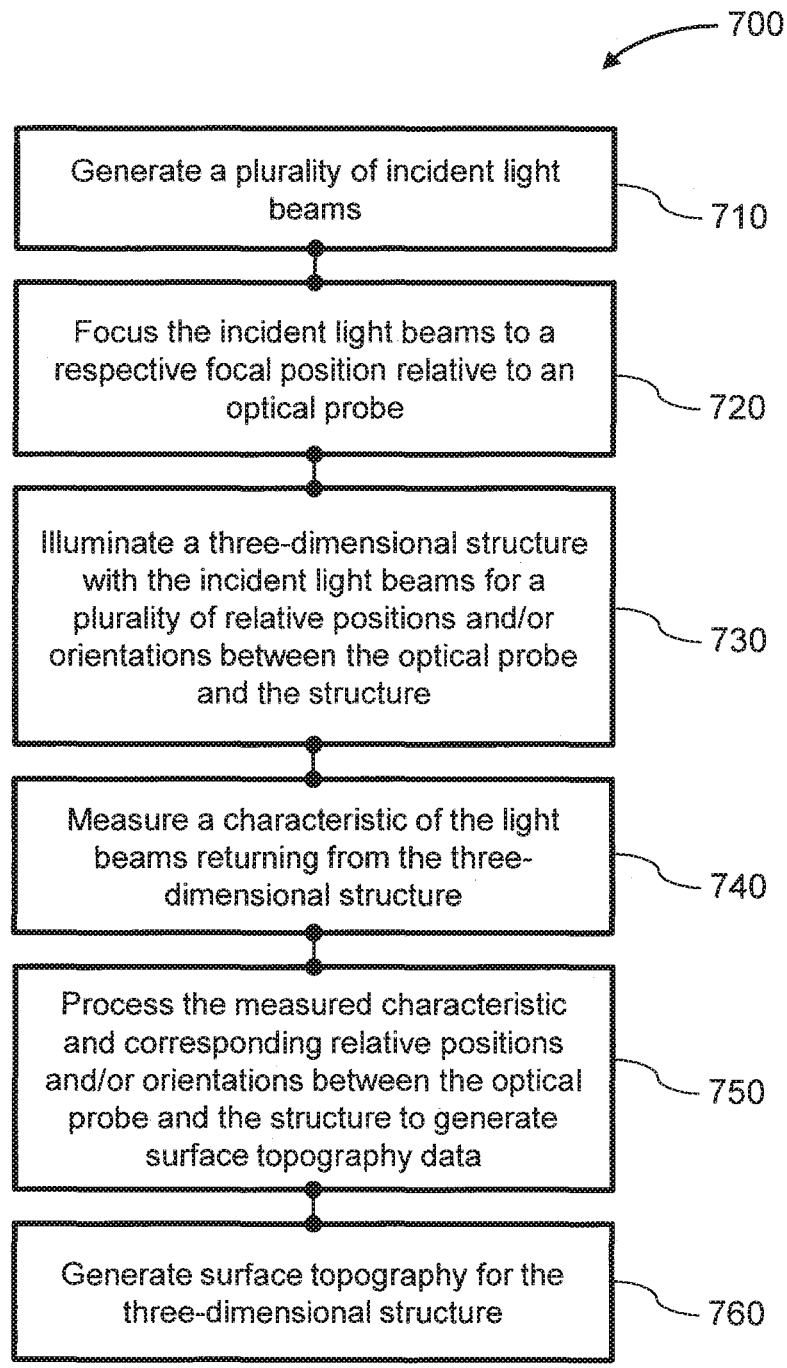
FIG. 8 is a simplified block diagram depicting acts of a method for measuring surface topography using fixed focal positions, in accordance with many embodiments.

FIG. 8 is a simplified block diagram depicting acts of a method 700 for measuring surface topography of a three-dimensional structure, in accordance with many embodiments. Any suitable optical devices or systems, such as the embodiments described herein, can be used to practice the method 700.

In act 710, a plurality of incident light beams is generated. In many embodiments, the optical device 22 can be used to form a two-dimensional pattern of light beams as described herein.

In act 720, each of the plurality of incident light beams is focused to a respective focal position relative to an optical probe. Any suitable focusing mechanism can be used, such as the embodiments described herein. In many embodiments, the light beams are focused to form a diagonal focal plane to provide Z scanning with motion of the probe, as previously described herein.

In act 730, a three-dimensional structure is illuminated with the incident light beams for a plurality of relative positions and/or orientations between the probe and the structure. In many embodiments, the light beams are focused to a diagonal focal plane such that movement of the probe through a plurality of positions and/or orientations relative to the structure enables three-dimensional scanning of the structure, as described herein. A plurality of returning light beams are produced by illuminating the structure with the incident light beams, with each returning light beam corresponding to an incident light beam.

In act 740, a characteristic of each of a plurality of light beams returning from the three-dimensional structure is measured. As previously mentioned, the characteristic can be any suitable measurable parameter of the light beams, such as intensity, wavelength, polarization, phase shift, interference, or dispersion. Any suitable device configured to measure the characteristic of each of the light beams can be used. For example, a suitable detector unit, such as a sensor (e.g., sensory array 68) including a two-dimensional array of sensor elements can be used, as previously described herein. The sensor array can be orthogonal or non-orthogonal to the returning light beams, based on the configuration of the focusing optics and the light source array.

In act 750, the measured characteristic and the corresponding relative positions and/or orientations between the optical probe and the structure are processed (e.g., by processor 24) to generate surface topography data for the structure. Any suitable method for processing the data of the measured characteristic can be used, such as the embodiments described herein. In many embodiments, the data of the measured characteristic is aligned based on data obtained by tracking the relative position and/or orientation of the optical probe (e.g., motion data and/or image data) as described herein.

In act 760, surface topography for the three-dimensional structure is generated, such as by the processor 24 as described herein. The resultant three-dimensional representation of the structure can be used for any suitable application, such as the dental and orthodontic procedures described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for measuring surface topography of a three-dimensional structure, the apparatus comprising:
    an optical probe moveable relative to the three-dimensional structure;
    an illumination unit configured to generate a plurality of incident light beams, each of the plurality of incident light beams comprising a first wavelength component;
    an optical system configured to focus the first wavelength component of each of the plurality of incident light beams to a respective fixed focal position relative to the optical probe while measuring the surface topography; and
    a detector unit configured to measure a plurality of returned light beams that are generated by illuminating the three-dimensional structure with the plurality of incident light beams in order to measure the surface topography.

2. The apparatus of claim 1, wherein the detector unit comprises a two-dimensional array of sensor elements from a corresponding returned light beam of the plurality of returned light beams.

3. The apparatus of claim 2, wherein the optical system is configured to form a two-dimensional pattern of the plurality of incident light beams from light generated by the illumination unit, the two-dimensional pattern of the plurality of incident light beams corresponding to the plurality of returned light beams measured by the two-dimensional array of sensor elements.

4. The apparatus of claim 3, wherein the optical system comprises an optics expander unit configured to expand light generated by the illumination unit to form the two-dimensional pattern of the plurality of incident light beams.

5. The apparatus of claim 2, wherein the illumination unit is configured to produce a two-dimensional pattern of the plurality of incident light beams corresponding to the plurality of returned light beams measured by the two-dimensional array of sensor elements.

6. The apparatus of claim 2, wherein:
the plurality of incident light beams are arranged in a plurality of rows having a first row and a last row;
incident light beams in each row are focused to a respective common focal length; and
the respective common focal lengths of the first row and the last row are different by a predetermined length.

7. The apparatus of claim 6, wherein the predetermined length is from 5 mm to 25 mm.

8. The apparatus of claim 2, wherein the two-dimensional array of sensor elements is arranged in a plane that is oriented for confocal sensing of the plurality of returned light beams relative to focal lengths of the first wavelength component of the plurality of incident light beams.

9. The apparatus of claim 8, wherein the plane of the two-dimensional array of sensor elements is non-orthogonal to the plurality of returned light beams.

10. The apparatus of claim 1, wherein the optical system is configured to focus the first wavelength component of the plurality of incident light beams to at least 10 different focal lengths relative to the scanner, and wherein the at least 10 different focal lengths have a range of at least 10 mm.

11. A method of measuring surface topography of a three-dimensional structure, the method comprising:
focusing a first wavelength component of each of a plurality of incident light beams to a respective fixed focal position relative to an optical probe while measuring the surface topography; and
measuring a plurality of returned light beams that are generated by illuminating the three-dimensional structure with the plurality of incident light beams for one or more of a plurality of different relative positions or a plurality of different orientations between the optical probe and the three-dimensional structure in order to measure the surface topography.

12. The method of claim 11, comprising tracking changes in one or more of relative position or orientation between the optical probe and the three-dimensional structure.

13. The method of claim 12, wherein:
the plurality of incident light beams are arranged in a plurality of rows having a first row and a last row;
incident light beams in each row are focused to a respective common focal length; and
the respective common focal lengths of the first row and the last row are different by a predetermined length.

14. The method of claim 13, wherein the predetermined length is at least 10 mm.

15. The method of claim 12, wherein the first wavelength component of the plurality of incident light beams is focused to at least 10 different focal lengths relative to the scanner, and wherein the at least 10 different focal lengths have a range of at least 10 mm.

16. The method of claim 11, further comprising generating the plurality of incident light beams.

17. The method of claim 16, wherein the measuring step is performed using a two-dimensional array of sensor elements, each sensor element of the two-dimensional array of sensor elements being configured to measure a corresponding returned light beam of the plurality of returned light beams.

18. The method of claim 17, wherein the plurality of incident light beams are generated as a two-dimensional pattern, and the two-dimensional pattern of the plurality of incident light beams corresponds to the plurality of returned light beams measured by the two-dimensional array of sensor elements.

* * * * *